United States Patent
Watson (10) Patent No.: US 7,397,035 B2
(45) Date of Patent: Jul. 8, 2008

(54) SCATTER CORRECTION FOR TIME-OF-FLIGHT POSITRON EMISSION TOMOGRAPHY DATA

(75) Inventor: Charles C. Watson, Knoxville, TN (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 127 days.

(21) Appl. No.: 11/581,527

(22) Filed: Oct. 16, 2006

(65) Prior Publication Data

US 2007/0085013 A1    Apr. 19, 2007

Related U.S. Application Data

(60) Provisional application No. 60/726,711, filed on Oct. 14, 2005.

(51) Int. Cl.
    *G01T 1/164* (2006.01)

(52) U.S. Cl. .............................. 250/363.07; 250/363.03
(58) Field of Classification Search ............ 250/363.01, 250/363.03, 363.04, 363.07
    See application file for complete search history.

(56) References Cited

U.S. PATENT DOCUMENTS

2005/0072929 A1* 4/2005 Chuang et al. ......... 250/363.03
2006/0163485 A1* 7/2006 Stearns et al. ......... 250/363.03

* cited by examiner

*Primary Examiner*—Constantine Hannaher
*Assistant Examiner*—Marcus H Taningco

(57) ABSTRACT

Correction of time-of-flight (TOF) PET data for scattered radiation explicitly models the TOF of the annihilation photon pairs along their individual scattered paths, yielding a distinct, accurate estimated scatter contribution for each time offset bin of the measured TOF data. This is accomplished by extending the single scatter simulation algorithm to include a new detection efficiency function $\epsilon_{TOF,n}$.

19 Claims, 5 Drawing Sheets

SCATTER CORRECTION FOR TIME-OF-FLIGHT POSITRON EMISSION TOMOGRAPHY DATA

CLAIM OF PRIORITY FROM RELATED APPLICATION

This application claims priority under 35 U.S.C. § 119(e) from Provisional Application Ser. No. 60/726,711, filed Oct. 14, 2005.

FIELD OF THE INVENTION

The present invention generally relates to nuclear medicine, and systems for obtaining nuclear medicine images. In particular, the present invention relates to systems and methods for reconstructing nuclear medicine images from time-of-flight (TOF) positron emission tomography (PET) data.

BACKGROUND OF THE INVENTION

Nuclear medicine is a unique medical specialty wherein radiation is used to acquire images which show the function and anatomy of organs, bones or tissues of the body. Radiopharmaceuticals are introduced into the body, either by injection or ingestion, and are attracted to specific organs, bones or tissues of interest. Such radiopharmaceuticals produce gamma photon emissions which emanate from the body and are captured by a scintillation crystal, with which the photons interact to produce flashes of light or "events." Events are detected by an array of photodetectors, such as photomultiplier tubes, and their spatial locations or positions are calculated and stored. In this way, an image of the organ or tissue under study is created from detection of the distribution of the radioisotopes in the body.

One particular nuclear medicine imaging technique is known as Positron Emission Tomography, or PET. PET is used to produce images for diagnosing the biochemistry or physiology of a specific organ, tumor or other metabolically active site. Measurement of the tissue concentration of a positron emitting radionuclide is based on coincidence detection of the two gamma photons arising from positron annihilation. When a positron is annihilated by an electron, two 511 keV gamma photons are simultaneously produced and travel in approximately opposite directions. Gamma photons produced by an annihilation event can be detected by a pair of oppositely disposed radiation detectors capable of producing a signal in response to the interaction of the gamma photons with a scintillation crystal. Annihilation events are typically identified by a time coincidence between the detection of the two 511 keV gamma photons in the two oppositely disposed detectors, i.e., the gamma photon emissions are detected virtually simultaneously by each detector. When two oppositely disposed gamma photons each strike an oppositely disposed detector to produce a time coincidence event, they also identify a line of response, or LOR, along which the annihilation event has occurred. An example of a PET method and apparatus is described in U.S. Pat. No. 6,858,847, which patent is incorporated herein by reference in its entirety.

Figure 1:
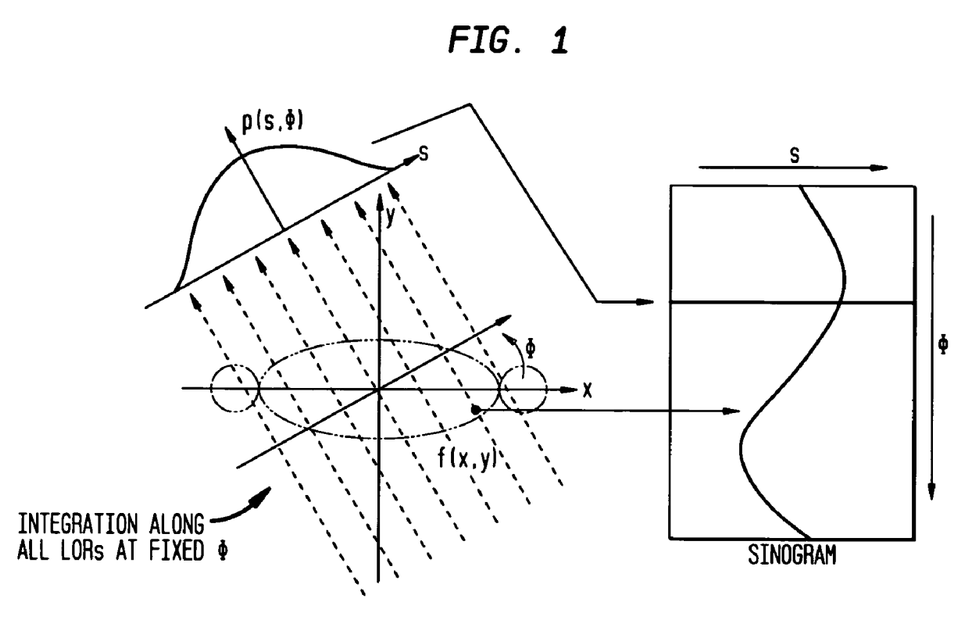
FIG. 1 is a diagram illustrating the relationship between PET projection data and a sinogram.

After being sorted into parallel projections, the LORs defined by the coincidence events are used to reconstruct a three-dimensional distribution of the positron-emitting radionuclide within the patient. In two-dimensional PET, each 2D transverse section or "slice" of the radionuclide distribution is reconstructed independently of adjacent sections. In fully three-dimensional PET, the data are sorted into sets of LORs, where each set is parallel to a particular detector angle, and therefore represents a two dimensional parallel projection $p(s, \phi)$ of the three dimensional radionuclide distribution within the patient, where s corresponds to the distance of the imaging plane perpendicular to the scanner axis and $\phi$ corresponds to the angle of the detector plane with respect to the x axis in (x, y) coordinate space (in other words, $\phi$ corresponds to a particular LOR direction). Coincidence events are integrated or collected for each LOR and stored as a sinogram. In this format, a single fixed point in f (x,y) traces a sinusoid in the sinogram. In each sinogram, there is one row containing the LORs for a particular azimuthal angle $\phi$; each such row corresponds to a one-dimensional parallel projection of the tracer distribution at a different coordinate along the scanner axis. This is shown conceptually in FIG. 1.

An event is registered if both crystals detect an annihilation photon within a coincidence time window $\tau$ (e.g., on the order of 4-5 ns), depending on the timing properties of the scintillator and the field of view. A pair of detectors is sensitive only to coincidence events occurring in the volume between the two detectors, thereby eliminating the need for physical collimation, and thus significantly increasing sensitivity. Accurate corrections can be made for the self-absorption of photons within the patient (i.e., attenuation correction) so that accurate measurements of tracer concentration can be made.

The number of time coincidences detected per second within a field of view (FOV) of a detector is the count rate of the detector. The count rate at each of two oppositely disposed detectors, A and B, can be referred to as singles counts, or singles, $S_A$ and $S_B$. The time required for a gamma photon to travel from its point of origin to a point of detection is referred to as the time of flight, or TOF, of the gamma photon. TOF is dependent upon the speed of light c and the distance traveled. A time coincidence, or coincidence event, is identified if the time difference between the arrival of signals in a pair of oppositely disposed detectors is within the coincidence time window $\tau$. In conventional PET, the coincidence detection time window $\tau$ is wide enough so that an annihilation event occurring anywhere within the object would produce annihilation gamma photons reaching their respective detectors within the coincidence window. Coincidence time windows of 4.5-12 nsec are common for conventional PET, and are largely determined by the time resolution capabilities of the detectors and electronics.

Figure 2:
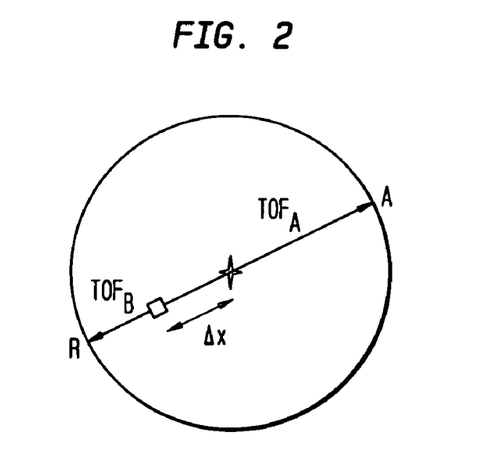
FIG. 2 is a diagram illustrating the concept of time of flight in PET imaging.

As illustrated in FIG. 2, if an annihilation event occurs at the midpoint of a LOR, the TOF of the gamma photon detected in detector A ($T_A$) is equal to the TOF of the gamma photon detected in detector B ($T_B$). If an annihilation event occurs at a distance $\Delta x$ from the midpoint of the LOR, the difference between $T_A$ and $T_B$ is $\Delta t = 2\Delta x/c$, where c is the speed of light. If d is the distance between the detectors, the TOF difference $\Delta t$ could take any value from $-d/c$ to $+d/c$, depending on the location of the annihilation event.

In contrast to conventional PET, time-of-flight positron emission tomography ("TOF-PET") is based on the measurement of the difference $\Delta t$ between the detection times of the two gamma photons arising from the positron annihilation event. This measurement allows the annihilation event to be localized along the LOR with a resolution of about 75-180 mm FWHM, assuming a time resolution of 500-1200 ps (picoseconds). Though less accurate than the spatial resolution of the scanner, this approximate localization is effective in reducing noise contributions both from random coincidence events and from true coincidences that actually originated elsewhere in the object. This improves both the stability of the reconstruction and the signal-to-noise ratio (SNR) in the final image, especially when imaging large objects. TOF- PET may increase image SNR by a factor of 2 or more compared to conventional PET.

TOF scanners developed in the early 1980s were used for research and clinical applications, but the SNR gain provided by the TOF measurements of about 500 ps resolution was offset by poorer spatial resolution and lower sensitivity due to the low stopping power of the $BaF_2$ and CsF scintillation crystals used in such scanners. Consequently, those TOF systems could not compete successfully with conventional (non-TOF) BGO scanners. As a result, TOF-PET almost completely disappeared from the scene in the 1990s. Today, faster electronics and crystals such as LSO and $LaBr_3$ reopen the prospect of exploiting the TOF information without compromising other parameters such as the count rate, the sensitivity, and the energy and spatial resolutions.

Figure 3:
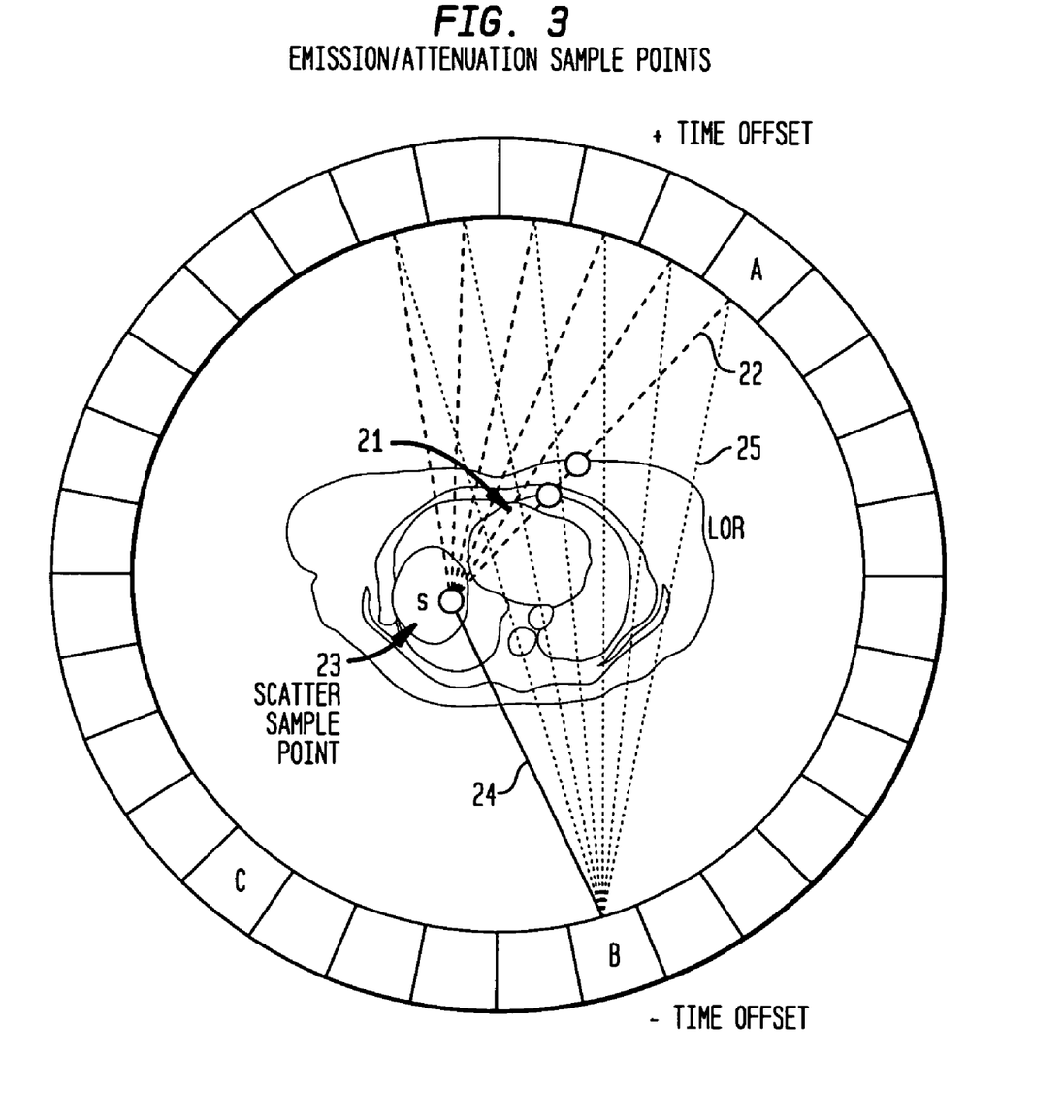
FIG. 3 is a diagram illustrating a single scatter simulation model for PET imaging using a ring detector, applicable for use with the present invention.

Septumless or "3D" PET scanners (i.e., without interplane septa) currently constitute a large percentage of the total market for PET imaging. Because of the lack of interplane septa, scattered events (i.e., annihilation photons undergoing Compton scattering before reaching the detector) may represent a large portion of the measured data (e.g., up to 50% or more in clinical studies). An example of such scatter is shown in FIG. 3, which illustrates a septumless PET scanner utilizing a ring detector configuration, which is also applicable for use with the present invention.

An annihilation event occurring at emission point 21 produces two oppositely traveling gamma photons along LOR 22. One of the gamma photons, however, may undergo Compton scattering at scatter point 23, which changes its travel direction to path 24. Consequently, while the first gamma photon is detected by detector A in line with the originating LOR 22, the scattered gamma photon will be detected in detector B, instead of by detector C. Consequently, the coincidence event detected in detectors A and C will result in a false LOR 25 being identified, instead of the correct LOR 22.

Accordingly, much effort has been devoted in the prior art to scatter correction techniques for conventional (i.e., non TOF) PET. With the broad coincidence time windows associated with conventional PET, the probability of detection of a scattered event does not depend significantly on the point of origin of the annihilation event along the LOR (see multiple points along LOR 22 in FIG. 3), and thus the scatter correction algorithm for conventional PET does not take into account the differential TOF of the scattered photon pair. The following articles are exemplary of the prior art development of the "single scatter simulation" (SSS) algorithm that is widely used in conventional PET:

1) J. S. Barney, J. G. Rogers, R. Harrop and H. Hoverath, "Object Shape Dependent Scatter Simulations," IEEE Trans. Nuc. Sci., 38, 719-725, 1991.

2) J. M. Ollinger and G. C. Johns, "Model-Based Scatter Correction for Fully 3D PET," 1993 IEEE Med. Img. Conf. Rec., 2, 1264-1268, 1994.

3) L. G. Hiltz and B. T. A. McKee, "Scatter correction for three-dimensional PET based on an analytic model dependent on source and attenuating object," Phys. Med. Biol., 39, 2059-2071, 1994.

4) J. M. Ollinger, "Model-Based Scatter Correction for Fully 3D PET," Phys. Med. Biol., 41, 153-176, 1996.

5) C. C. Watson, D. Newport and M. E. Casey, "A Single Scatter Simulation Technique for Scatter Correction in 3D PET," in Three-Dimensional Image Reconstruction in Radiology and Nuclear Medicine, P. Grangeat and J.-L. Amans (eds.), Kluwer Academic Publishers, Dordrecht, 1996, pp. 255-268.

6) C. C. Watson, D. Newport, M. E. Casey, R. A. deKemp, R. S. Beanlands, and M. Schmand, "Evaluation of simulation-based scatter correction for 3-D PET cardiac imaging," IEEE Trans. Nuc. Sci., vol. 44, pp. 90-97, February 1997.

7) C. C. Watson, "New, faster, image-based scatter correction for 3D PET," IEEE Trans. Nucl. Sci., vol. 47, pp. 1587-94, 2000.

8) Werling A, Bublitz O, Doll J, Adam L E, Brix G, "Fast implementation of the single scatter simulation algorithm and its use in iterative image reconstruction of PET data," Phys Med Biol., 47, 2947-60, 2002

9) Watson C C, Casey M E, Michel C, Bendriem B. "Advances in scatter correction for 3D PET/CT." In: 2004 IEEE Nuclear Science Symposium Conference Record [book on CD-ROM]. Piscataway, N.J.: IEEE; 2004:M5-166.

10) Accorsi R, Adam L E, Werner M E, Karp J S, "Optimization of a fully 3D single scatter simulation algorithm for 3D PET," Phys Med Biol., 49, 2577-98, 2004.

However, it is to be expected that scatter correction techniques developed for conventional PET may not be adequate for TOF PET, particularly those model-based algorithms that simulate scatter contributions. This is because the scattered and unscattered radiation follow distinct paths through the object, and therefore, for a given time offset, the portion of the emission distribution that may contribute to a detector pair is distinct for the scattered and unscattered radiation. Thus the scatter contribution to a given LOR may vary with time offset differently than the variation in true (unscattered) coincidences. An accurate scatter correction algorithm must correctly account for the time offsets of detected scattered photon pairs.

The following articles are the only prior art that the inventor is currently aware of that discuss scatter correction for TOF-PET. They propose algorithms that are quite different from the method provided by the present invention:

B Bendriem, F Soussaline, R Campagnolo, B Verrey, P Wajngerg, and A Syrota, "A Technique for the Correction of Scattered Radiation in a PET System Using Time-of-Flight Information," J. Comput. Assist. Tomgr., 10, 287-295, 1986.

M Conti, B Bendriem, M Casey, M Chen, F Kehren, C Michel and V Panin, "Implementation of Time-Of-Flight on CPS HiRez PET scanner." In: 2004 IEEE Nuclear Science Symposium Conference Record [book on CD-ROM]. Piscataway, N.J.: IEEE; 2004:M3-1.

M Conti, B Bendriem, M Casey, M Chen, F Kehren, C Michel and V Panin, "First experimental results of time-of-flight reconstruction on an LSO PET scanner." Phys. Med Biol., vol. 50, pp. 4507-4526, 2005.

SUMMARY OF THE INVENTION

The present invention solves the existing need in the art by providing an accurate scatter correction method for TOF-PET, thereby permitting quantitative image reconstruction from TOF-PET data without artifacts caused by inclusion of scatter data.

According to one embodiment, the invention provides a method of correcting for scatter in time-of-flight (TOF) PET data from an object, including the steps of determining a plurality of TOF time-offset bins, estimating a detection efficiency function for each of the plurality of TOF time-offset bins, estimating a single scatter coincidence rate in a pair of PET detectors over a volume of the object for each of said TOF time-offset bins by using a corresponding detection efficiency function in a single scatter simulation algorithm, and subtracting estimated scatter amounts resulting from the estimated single scatter coincidence rate from measured TOF PET data in each of the TOF time-offset bins.

BRIEF DESCRIPTION OF THE DRAWINGS

The invention will now be more fully described by way of example with reference to the accompanying drawings in which.

DETAILED DESCRIPTION OF THE INVENTION

The present invention will now be described and disclosed in greater detail. It is to be understood, however, that the disclosed embodiments are merely exemplary of the invention and that the invention may be embodied in various and alternative forms. Therefore, specific structural and functional details disclosed herein are not to be interpreted as limiting the scope of the claims, but are merely provided as an example to teach one having ordinary skill in the art to make and use the invention.

As explained above, in conventional PET, the integrals through the emission image along rays of travel from a scatter point to a detector, such as $\int_S^B \lambda(s) ds$, do not depend on the LOR with which they are associated. Since each such ray is associated with many LORs, as illustrated in FIG. 3, the numerical computation of the scatter rate can be made more efficient by computing each ray integral only once, and then simply reusing this value whenever the scatter contribution to an associated LOR is evaluated.

In the conventional (non-TOF) SSS algorithm, the expected single-scatter coincidence rate in the detector pair (A,B), due to scatter in the object, is estimated as the volume integral of a scattering kernel over the scattering medium according to:

$$S^{AB} = \int_{V_s} dV_s \left( \frac{\sigma_{AS}\sigma_{BS}}{4\pi R_{AS}^2 R_{BS}^2} \right) \frac{\mu}{\sigma_c} \frac{d\sigma_c}{d\Omega} [I^A + I^B] \quad (1)$$

Where $$I^A = \varepsilon_{AS}\varepsilon'_{BS} e^{-\left(\int_S^A \mu ds + \int_S^B \mu' ds\right)} \int_S^A \lambda(s) ds$$

$$I^B = \varepsilon_{BS}\varepsilon'_{AS} e^{-\left(\int_S^A \mu' ds + \int_S^B \mu ds\right)} \int_S^B \lambda(s) ds$$

With respect to Equation (1), referring to FIG. 3, Vs is the scatter volume, S is the scatter point, s is the distance along a ray such as AS, $\sigma_{AS}$ is the geometrical cross section of detector A for γ-rays incident along AS, $R_{AS}$ is the distance from S to A, $\varepsilon_{AS}$ is the efficiency of detector A for γ-rays incident along AS, μ is the linear attenuation coefficient, λ is the emitter density in the object, $\sigma_c$ is the total Compton interaction cross section, and Ω is the scattering solid angle. λ and μ are determined from preliminary estimated emission and transmission image volumes, respectively. The differential scattering cross-section, $d\sigma_c/d\Omega$, is computed from the Klein-Nishina formula.

In TOF PET tomography, however, one additionally measures the arrival-time difference of the two detected photons arising from an annihilation event. This time offset depends both on the position of the emission point along the ray, as well as the difference in length of the two rays forming one scatter path (e.g., ASB). The differential time of flight is measured with some instrumental time resolution and discrete sampling interval. Consequently, for each resulting time offset bin, indexed by n, there is a unique detection probability factor that depends in a non-separable way on the emission point and the LOR. This TOF effect may be incorporated into the SSS model above by introducing a new detection efficiency function, $\varepsilon_{TOF,n}$ into the emission line integrals according to:

$$S_{TOF,n}^{AB} = \int_{V_s} dV_s \left( \frac{\sigma_{AS}\sigma_{BS}}{4\pi R_{AS}^2 R_{BS}^2} \right) \frac{\mu}{\sigma_c} \frac{d\sigma_c}{d\Omega} [I_{TOF,n}^A + I_{TOF,n}^B] \quad (2)$$

$$I_{TOF,n}^A = \varepsilon_{AS}\varepsilon'_{BS} e^{-\left(\int_S^A \mu ds + \int_S^B \mu' ds\right)} \int_S^A \varepsilon_{TOF,n}[(R_{BS} - R_{AS})/2 + s]\lambda(s) ds$$

$$I_{TOF,n}^B = \varepsilon_{BS}\varepsilon'_{AS} e^{-\left(\int_S^A \mu' ds + \int_S^B \mu ds\right)} \int_S^B \varepsilon_{TOF,n}[(R_{BS} - R_{AS})/2 - s]\lambda(s) ds$$

Since the line integrals are now coupled with the LOR, they cannot be pre-computed in the same way as for the non-TOF case, thereby reducing the efficiency of the calculation somewhat.

A time of flight difference of Δt nanoseconds is equivalent to a spatial offset of the emission point from the midpoint of the scatter path, in centimeters, of Δx=cΔt/2, where c is the speed of light (approximately 30 cm/nsec). In the following the differential TOF is referred to in terms of spatial distance using this conversion relation.

Figure 4:
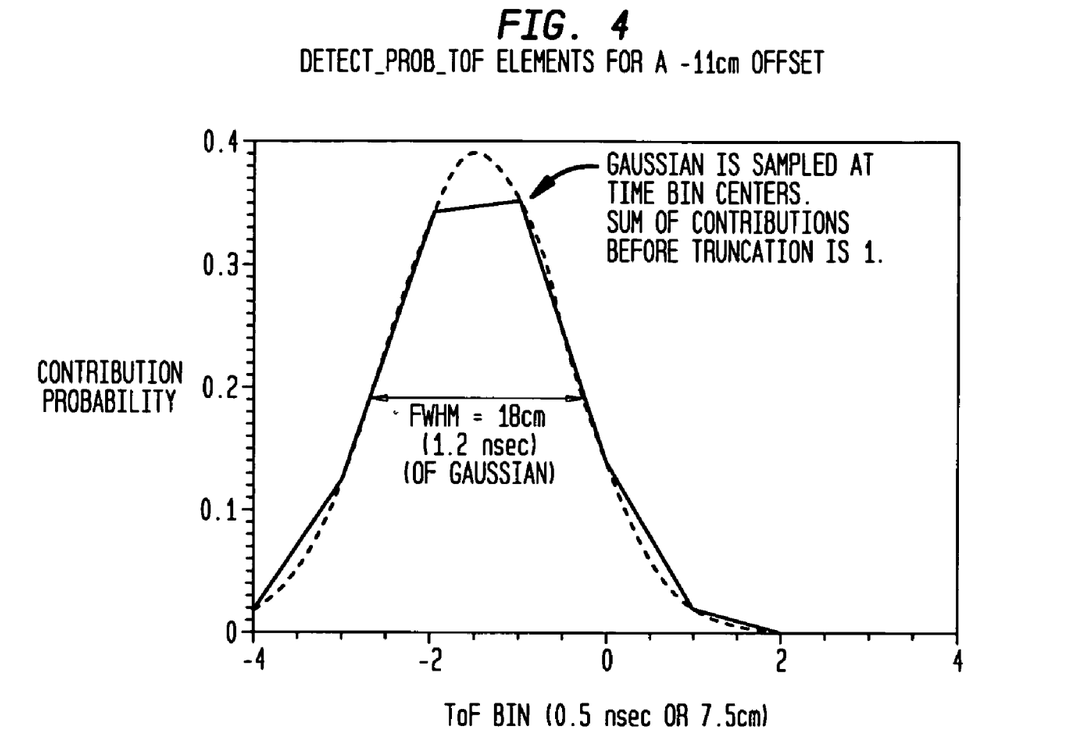
FIG. 4 is a graph illustrating a time detection probability model for 1.2 nsec resolution and a 0.5 nsec sampling interval.

It is common practice to model the TOF detection probability function for unscattered radiation by sampling a Gaussian distribution. Strictly speaking, this is incorrect for discretely sampled data since the sum of probabilities thus computed do not add to 1. More correctly, one can model the detection efficiency as a quasi-Gaussian distribution. Let the TOF sampling bin width be τ, and the bin index, n, range from −N/2 to +N/2, where N is the total number of measured TOF bins. Then the probability that a detected emission event at an offset of Δx will be recorded in the nth TOF bin is:

$$\varepsilon_{TOF,n}(\Delta x) = \frac{e^{-\frac{(\Delta x - n\tau)^2}{2\sigma^2}}}{\sum_{n'} e^{-\frac{(\Delta x - n'\tau)^2}{2\sigma^2}}} \quad (3)$$

where the sum in the denominator is extended over all possible TOF bins (whether measured or not). This functions models the convolution of the intrinsic TOF resolution function with the square function representing a TOF bin. Its full width at half maximum (FWHM) is related to $\sigma$ by $FWHM^2=(4\ln 2)2\sigma^2$. An example of this function is shown in FIG. 4 for $\Delta x=-11$ cm (0.73 nsec), FWHM=18 cm (1.2 nsec), $\tau=7.5$ cm (0.5 nsec), and N=9. Of course, a different function could be used to model $\epsilon_{TOF,n}$ if there were physical justification for it.

Once the scatter is estimated according to Equation (2), the measured PET emission data can be corrected for scatter by subtracting this contribution. Equation (2) can be evaluated numerically using a variety of different algorithms. The approach used for the present implementation is described below.

Equation (2) is formulated as a volume integral over scatter position. This is implemented as a sum of contributions over a set of sample scatter points. Thus, scatter sample points are distributed quasi-randomly throughout the volume of the object. Detectors are sampled uniformly on a ring surrounding the object, as illustrated in FIG. 3. Each combination of detector pair (such as A, B) and scatter point (such as S) define a scatter path contribution to the volume integral that must be computed by evaluating the appropriate line integrals along the two segments, or rays, of the path (i.e., segment AS and segment SB). These ray integrals in turn are evaluated as a sum over samples of the preliminary estimated images of the object at discrete steps along the ray. The ray integrals through the transmission image ($\mu$) do not depend on the LOR and can still be pre-computed. The ray integrals through the emission image ($\lambda$), however, give distinct contributions for different LORs, due to the presence of $\epsilon_{TOF,n}$, and must be re-computed for each scatter path (technically, it is possible to pre-compute the emission ray integrals for a variety of potential time offsets, and then interpolate these to estimate each desired integral, but this is unlikely to be more efficient numerically).

To evaluate the ray integrals, the images are sampled at a uniform step interval along the ray as indicated in FIG. 3. For the emission image, these samples are weighted by the scoring efficiency for each TOF bin, $\epsilon_{TOF,n}(\Delta X)$, and these weighted samples are summed to give the contribution for that ray integral to the scatter for each TOF bin. At each sample point, $\Delta x$ is determined as either $(R_{BS}-R_{AS})/2+s$ (for AS) or $(R_{BS}-R_{AS})/2-s$ (for BS), where s is the distance of the sample point along the ray from S. This is in keeping with a convention that time offsets in the projection direction are positive.

To make the calculation more efficient, the detection efficiencies $\epsilon_{TOF,n}(\Delta x)$ are pre-computed as a scoring table by evaluating them on a fine grid (typically 1 cm) in $\Delta x$ for each TOF bin n, and then using nearest neighbor sampling for $\Delta x$ when evaluating $\epsilon_{TOF,n}(\Delta x)$ in the ray integral calculations.

In both the TOF and non-TOF SSS algorithms, scatter and ray sample points are defined relative to the transaxial plane of the detector ring and their positions are pre-computed and stored as pointer offsets into the image arrays. The sample points for each detector ring are then obtained simply by axially shifting the location of the reference pointer into the arrays. This has the effect of axially translating the sample points relative to the image. The re-use of these pointers gives a very significant improvement in the numerical efficiency of the SSS algorithm.

Figure 5:
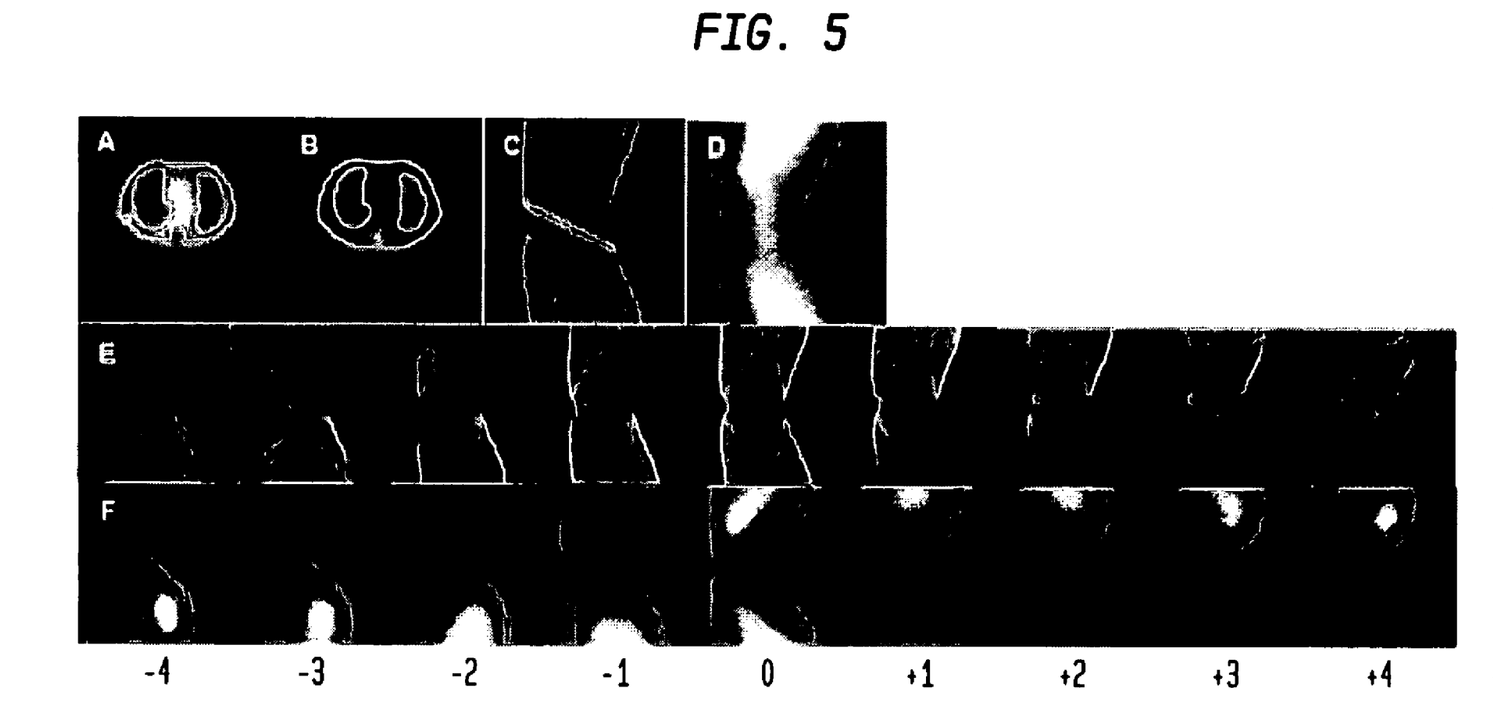
FIG. 5 is a composite diagram illustrating TOF-SSS emission and scatter sinograms in accordance with the present invention.
Figure 6:
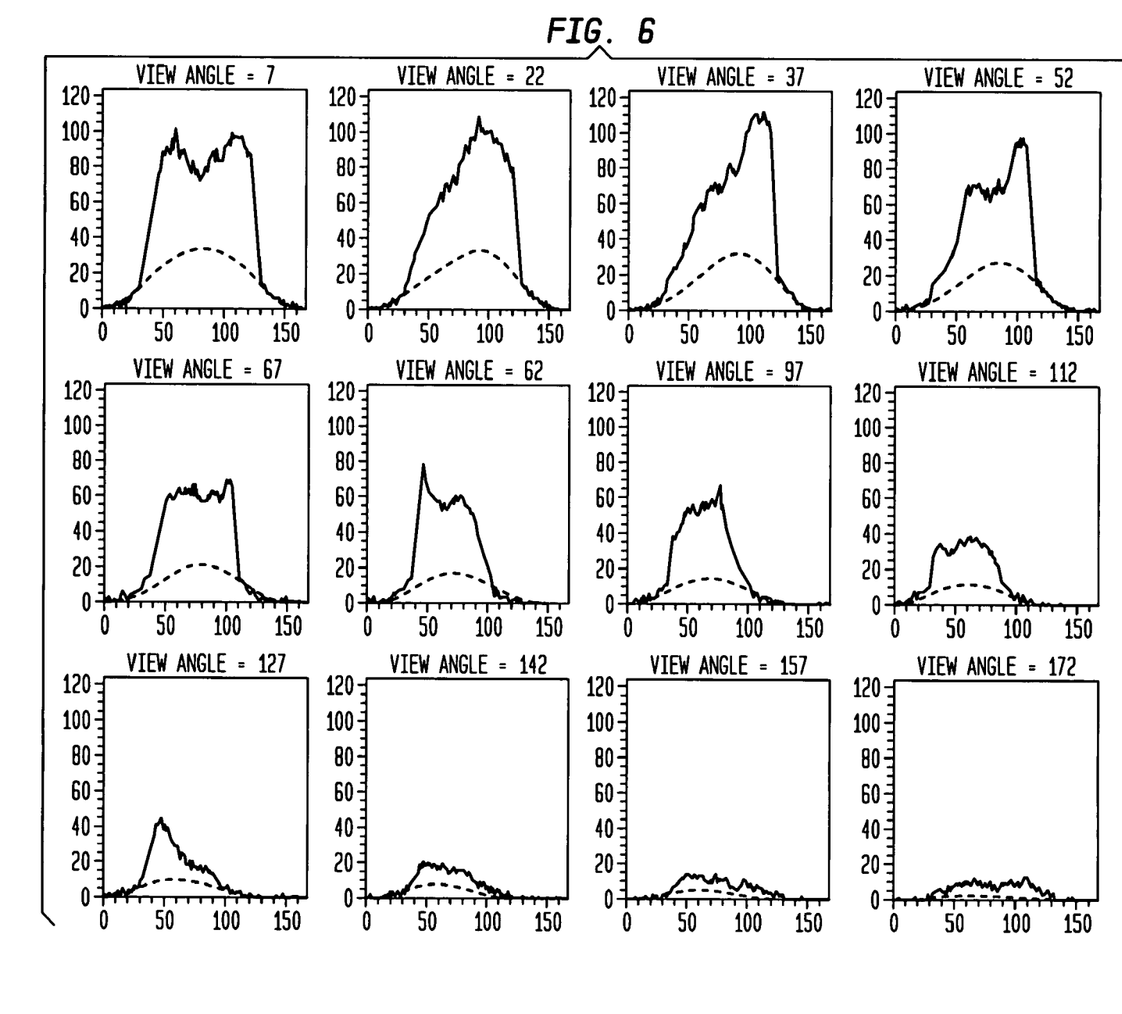
FIG. 6 is a composite diagram illustrating sinogram profiles at 12 projection angles for the sinograms of FIG. 5, time bin +3, where the solid lines indicate measured emission data and the dashed lines indicate computed scatter.

The TOF-SSS scatter computation and correction algorithm described above has been implemented in software. Scatter sinograms estimated according to this algorithm are compared to measured emission data in FIGS. 5 and 6, for a torso phantom study. In FIG. 5, (A) is an emission image of a torso phantom, central plane; (B) is a transmission (CT) image of the same; (C) is an image of measured net "trues" sinogram summed over planes and time bins (non-TOF); (D) is an image of computed scatter sinogram summed over planes and time bins; (E) shows measured TOF sinograms summed over planes; and (F) shows computed TOF scatter sinograms. The time offset bins are indicated along the bottom of FIG. 5 and are 0.5 nsec wide. It can be seen that there is very significant variation in the scatter distribution with TOF offset, but that the simulation accurately follows the trends of the TOF emission data. This level of accuracy is necessary to take full advantage of the capabilities of PET for quantitative clinical TOF imaging.

It should be appreciated by those having ordinary skill in the art that while the present invention has been illustrated and described in what is deemed to be the preferred embodiments, various changes and modifications may be made to the invention without departing from the spirit and scope of the invention. For example, it will be recognized by those skilled in the art that certain reconstruction algorithms such as maximum likelihood or maximum a posteriori estimation may include the scatter estimate in a forward model of the data rather than pre-correcting the data by subtracting the scatter component. Therefore, it should be understood that the present invention is not limited to the particular embodiments disclosed herein.

What is claimed is:

1. A method of correcting for scatter time-of-flight (TOF) PET data measured from an object, comprising the steps of determining a plurality of TOF time-offset bins, estimating a detection efficiency function for each of said plurality of TOF time-offset bins, estimating a single scatter coincidence rate in a pair of PET detectors over a volume of said object for each of said TOF time-offset bins by using a corresponding detection efficiency function in a single scatter simulation algorithm, and using estimated scatter amounts resulting from said estimated single scatter coincidence rate to reduce the effect of scatter on measured TOF-PET data in each of said TOF time-offset bins.

2. The method of claim 1, wherein said estimated scatter amounts resulting from said estimated single scatter coincidence rate are subtracted from measured TOF PET data in each of said TOF time-offset bins.

3. The method of claim 1, wherein said estimated scatter amounts resulting from said estimated single scatter coincidence rate are included in a forward model of measured TOF PET data in each of said TOF time-offset bins.

4. The method of claim 1, wherein said detection efficiency function is a probability weighting function.

5. The method of claim 4, wherein said probability weighting function is modeled as a Gaussian function.

6. The method of claim 5, wherein said Gaussian function is a quasi-Gaussian function.

7. The method of claim 6, wherein said quasi-Gaussian function is normalized.

8. The method of claim 7, wherein said quasi-Gaussian function is sampled.

9. The method of claim 1, wherein said plurality of TOF time-offset bins comprises n bins, where n is an integer, and said detection efficiency function is of the form:

$$\varepsilon_{TOF,n}(\Delta x) = \frac{e^{\frac{(\Delta x - n\tau)^2}{2\sigma^2}}}{\sum_{n'} e^{\frac{(\Delta x - n'\tau)^2}{2\sigma^2}}}$$

10. The method of claim 1, wherein said single scatter simulation algorithm including said detection efficiency function is of the form $$S_{TOF,n}^{AB} = \int_{V_S} dV_S \left( \frac{\sigma_{AS}\sigma_{BS}}{4\pi R_{AS}^2 R_{BS}^2} \right) \frac{\mu}{\sigma_c} \frac{d\sigma_c}{d\Omega} [I_{TOF,n}^A + I_{TOF,n}^B]$$

$$I_{TOF,n}^A = \varepsilon_{AS} \varepsilon'_{BS} e^{-(\int_S^A \mu ds + \int_S^B \mu' ds)} \int_S^A \varepsilon_{TOF,n}[(R_{BS} - R_{AS})/2 + s]\lambda(s) ds$$

$$I_{TOF,n}^B = \varepsilon_{BS} \varepsilon'_{AS} e^{-(\int_S^A \mu' ds + \int_S^B \mu ds)} \int_S^B \varepsilon_{TOF,n}[(R_{BS} - R_{AS})/2 - s]\lambda(s) ds.$$

11. The method of claim 1, wherein detection efficiencies $\varepsilon_{TOF,n}(\Delta x)$ are pre-computed for each TOF time-offset bin n on a grid for $\Delta x$.

12. The method of claim 11, wherein said grid is on the order of 1 cm.

13. The method of claim 11, further comprising the step of using nearest neighbor sampling for $\Delta x$ when evaluating $\epsilon_{TOF,n}(\Delta x)$ in the single scatter simulation integral.

14. A computer readable storage medium having stored thereon a plurality of computer-executable instructions for correcting for scatter time-of-flight (TOF) PET data measured from an object, comprising instructions for:
  determining a plurality of TOF time-offset bins;
  estimating a detection efficiency function for each of said plurality of TOF time-offset bins;
  estimating a single scatter coincidence rate in a pair of PET detectors over a volume of said object for each of said TOF time-offset bins by using a corresponding detection efficiency function in a single scatter simulation algorithm; and
  using estimated scatter amounts resulting from said estimated single scatter coincidence rate to reduce the effect of scatter on measured TOF-PET data in each of said TOF time-offset bins.

15. The method of claim 14, wherein said estimated scatter amounts resulting from said estimated single scatter coincidence rate are subtracted from measured TOF PET data in each of said TOF time-offset bins.

16. The method of claim 14, wherein said estimated scatter amounts resulting from said estimated single scatter coincidence rate are included in a forward model of measured TOF PET data in each of said TOF time-offset bins.

17. A time-of-flight (TOF) PET imaging apparatus, comprising:
  a plurality of detectors for measuring TOF PET data from an object undergoing imaging, and
  a processor for correcting for scatter said measured TOF PET data using a single scatter simulation algorithm including a detection efficiency function for each of a plurality of TOF time-offset bins; whereby a single scatter coincidence rate in a pair of PET detectors is estimated over a volume of said object for each of said TOF time-offset bins by using a corresponding detection efficiency function in a single scatter simulation algorithm, and estimated scatter amounts resulting from said estimated single scatter coincidence rate are used to reduce the effect of scatter on measured TOF-PET data in each of said TOF time-offset bins.

18. The method of claim 17, wherein said estimated scatter amounts resulting from said estimated single scatter coincidence rate are subtracted from measured TOF PET data in each of said TOF time-offset bins.

19. The method of claim 17, wherein said estimated scatter amounts resulting from said estimated single scatter coincidence rate are included in a forward model of measured TOF PET data in each of said TOF time-offset bins.

* * * * *